United States Patent [19]

Glover et al.

[11] 4,121,468

[45] Oct. 24, 1978

[54] METHOD AND APPARATUS FOR REFLECTIVE ULTRASONIC IMAGING UTILIZING RECONSTRUCTION OF ACOUSTIC IMPEDANCE PROJECTIONS

[75] Inventors: Gary H. Glover, Waukesha, Wis.; Frank L. Lederman, Schenectady, N.Y.

[73] Assignee: General Electric Company, Schenectady, N.Y.

[21] Appl. No.: 809,080

[22] Filed: Jun. 23, 1977

[51] Int. Cl.$^2$ .............................................. G01N 29/04
[52] U.S. Cl. ....................................... 73/602; 73/622; 73/626; 128/2 V
[58] Field of Search .................. 73/602, 618, 620, 621, 73/622, 625, 626; 340/5 MP; 128/2 V, 2.05 Z; 364/507; 250/312

[56] References Cited

U.S. PATENT DOCUMENTS

| | | | |
|---|---|---|---|
| 3,673,394 | 6/1972 | Hartmann | 73/618 |
| 3,830,223 | 8/1974 | Beretsky et al. | 128/2 V |
| 3,934,458 | 1/1976 | Beretsky et al. | 73/67.9 |
| 4,074,564 | 2/1978 | Anderson | 73/596 |

OTHER PUBLICATIONS

J. F. Greenleaf et al., Algebraic Reconstruction of Spatial Distributions of Acoustic Velocities in Tissue from Their Time of Flight Profiles, Acoustic Holography, vol. 6, 1975, Plenum Press, pp. 71-90.

*Primary Examiner*—Richard C. Queisser
*Assistant Examiner*—John P. Beauchamp
*Attorney, Agent, or Firm*—Donald R. Campbell; Joseph T. Cohen; Marvin Snyder

[57] ABSTRACT

An ultrasonic imaging system for medical and industrial applications produces quantitative acoustic impedance distributions from reflection data. The method and scanner apparatus with analog computation circuitry herein described acquires echo pulses reflected from impedance discontinuities in the specimen and computes impedance projections. The ensemble of projections, as in other computerized tomography systems, is used for reconstruction of the images which in this case are impedance distributions in a thin slice of the specimen.

15 Claims, 7 Drawing Figures

METHOD AND APPARATUS FOR REFLECTIVE ULTRASONIC IMAGING UTILIZING RECONSTRUCTION OF ACOUSTIC IMPEDANCE PROJECTIONS

BACKGROUND OF THE INVENTION

This invention relates to a method and apparatus for reflective ultrasonic imaging in medical and industrial applications. More particularly, the invention relates to an ultrasonic scanner with associated circuitry and to a method for generating acoustic impedance projections from reflection data in a computerized reconstruction tomography system.

Conventional ultrasonic imaging systems including those operating in B-scan mode do not provide quantitative information pertaining to a bulk, constitutively significant property of the imaged specimen or object. The deficiencies in such systems result mainly from direct utilization of the echo amplitude as the imaged quantity. The amplitude in turn is modulated in a complicated fashion by reflection, refraction, diffuse diffractive scattering, and bulk attenuation. Thus, the images portray interfacial geometry but cannot be quantified in terms of any simple bulk specimen property.

It is, however, desirable in both medical and nondestructive testing environments to have an accurate, quantitative measure of the bulk specimen properties. This desirability has been borne out amply by recent experience in medical x-ray tomography. Time-of-flight (TOF) computerized tomography is one ultrasonic technique which provides quantitative reconstructions of acoustic velocity distributions. For further information, reference may be made to copending application Ser. No. 716,109 filed on Aug. 20, 1976 by Gary H. Glover, now U.S. Pat. No. 4,075,883 entitled "Ultrasonic Fan Beam Scanner for Computerized Time-of-Flight Tomography", and assigned to the same assignee as this invention. The system generates numeric values indicative of the acoustic velocity at known coordinates in a specimen layer, which can be displayed in numeric printout form or as a video image by gray scale or pseudo-color encoding the various velocity values. In noninvasive breast examination, tumorous tissue is readily distinguished from normal tissue on the basis of the computed velocity values. However, time-of-flight tomography is limited to only these few portions of the anatomy which allow transmission through the specimen from a number of angles.

The principal object of the present invention is to realize an ultrasonic imaging system and method based on reflection which yields quantitative data, to thus combine the advantages of reflection systems (one-port viewing) with computerized transmission systems (quantitative results).

SUMMARY OF THE INVENTION

To realize reflective ultrasonic imaging of quantitative values of impedance distributions, echo signals are acquired and analyzed to obtain acoustic impedance projections. Echo signals are received whenever there is a discontinuity in acoustic impedance in the specimen. The projection of the impedance is defined as the line integral of the impedance from the transducer to a predetermined maximum time or depth. The equation is given later, and has as terms the echo signal amplitude, the square of time effectively measured from the generation of an acoustic pulse, a known acoustic loss factor which increases as the depth into the specimen increases, a known system impulse response or calibration factor, and the maximum time or upper limit of integration. In a manner analogous to x-ray and time-of-flight ultrasound computerized tomography, an ensemble of projections is obtained to be used in combination to reconstruct impedance distributions at known coordinates in a specimen layer. Impedance is a bulk, constitutively significant parameter of the specimen or object and supplies useful information in both medical and industrial imaging applications.

In practicing the method, one or more electroacoustic transducers is excited sequentially to generate a series of acoustic pulses which propagate along multiple paths through the specimen sufficient to scan the specimen for a single projection. Echo pulses reflected at impedance discontinuities are detected to thereby generate a received echo electrical signal for each path. The echo signals are processed and impedance projection output data representing the line integral of the impedance along the path is computed. The foregoing steps are repeated at multiple scan angles of the excited transducers relative to the specimen to derive additional sets of impedance projection output data for other projections.

The preferred embodiment of an apparatus for producing impedance projections includes an ultrasound scanner with a linear scan or fan beam scan geometry, and an analog computation circuit capable of generating data in real time. Additional features are a memory to store the projection data and provision for translating the scanner in the axial direction to acquire data to image impedance distributions at a plurality of parallel specimen layers.

DESCRIPTION OF THE PREFERRED EMBODIMENTS

Figure 1:
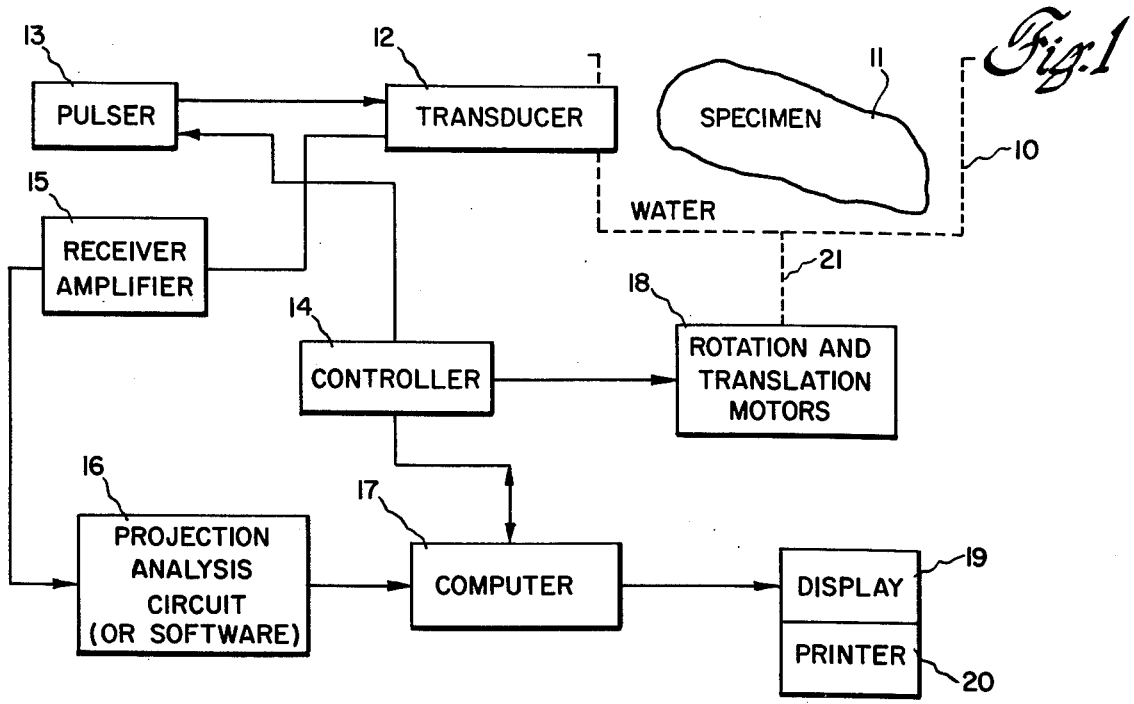
FIG. 1 is a simplified diagram of a reflective ultrasonic imaging system to provide quantitative acoustic impedance distributions from reflection data.

In the reflective ultrasonic imaging system in FIG. 1, reflected energy is analyzed by a computer to yield highly quantitative reconstructions of the two-dimensional acoustic impedance distributions within a thin slice of the object or specimen. The concept is similar to other computerized reconstruction tomography systems, e.g., x-ray and time-of-flight ultrasound systems, in that an ensemble of projections is utilized to digitally form the image. The exemplary embodiment comprises a motorized ultrasound scanner to acquire echo traces from the object or specimen, and a means of analyzing the echo data, either analog or digital, to obtain acoustic impedance projections. As in other tomography systems, a computer is employed to reconstruct and display the acoustic impedance distributions. The imaging system has numerous applications, such as whole body medical imaging and the nondestructive testing of metal parts.

The reflective ultrasonic imaging system will first be discussed briefly with reference to the simplified diagram in FIG. 1. The ultrasound scanner is comprised of a tank 10 filled with water or other liquid in which is immersed the object or specimen 11 being examined. The tank supports one or more electroacoustic transducers 12 which function both as transmitter and receiver. Echoes are received whenever there is an acoustic impedance discontinuity. For a given scan angle, a single transducer 12 is mechanically scanned and a received echo signal is generated at each transducer position; alternatively a transducer array remains stationary and the individual transducers are electrically operated in sequence to generate the received echo signals. This provides data for a "view" of the object from which a single impedance projection can be computed. More particularly, a pulser 13 upon being actuated by a controller 14 generates a steeply rising electrical pulse that is applied to and excites transducer 12, which is typically a piezoelectric transducer. The generated acoustic pulse is reflected at the front and back surfaces of object 11 and at every impedance discontinuity within the object, and the echo pulses are detached by the transducer and a corresponding received echo electrical signal is generated. After being amplified by a receiver amplifier 15, the received echo signal is fed to a projection analysis circuit 16, either analog or digital, where the echo trace is processed and impedance projection output data representing the line integral of the acoustic impedance along the path is computed. As the transducer is scanned, many such projection values are obtained to form the impedance projection of the specimen. The ensemble of the projection output data for a single impedance projection is stored in a memory or a computer 17. Instead of analyzing the echo signals in projection analysis circuit 16 to obtain impedance projection output data, the received echo signals can be digitized and fed to a computer along with other information required to compute the line integral of acoustic impedance along the path (i.e., either a hardware or software approach to projection analysis is possible, although the latter is not further explained here).

The angle of the scan is then varied systematically by means of rotation motor 18, and other projections similarly obtained and stored in the computer. This data is of exactly the same form as in other computerized reconstruction systems, namely ensembles of line integrals. The usual reconstruction algorithms, such as the convolution algorithm, can be applied to obtain the integrand in two-dimensional space, in this case, acoustic impedance. The computed results for a thin slice of the specimen are formulated as impedance values assigned to picture elements or pixels in a coordinate system encompassing the specimen region. A video image may be obtained by grey scale or pseudo-color encoding of the various impedance values on a cathode ray tube display device 19. Alternatively, the impedance values can be printed out in a similar arrangement of rows and columns using a printer 20. General information on reconstruction techniques and imaging is given in the article "Image Reconstruction from Projections", Scientific American, Vol. 233, No. 4, October 1975, pp. 56-68. In order to image parallel layers or slices of the specimen, translation motor 18 is operated to translate tank 10 and transducer 12 in the direction of rotational axis 21, the specimen remaining stationary. The foregoing sequence is repeated, scanning the specimen at many scan angles to acquire sets of received echo signals which are analyzed to obtain additional sets of impedance projections to be used in combination to reconstruct impedance distributions in the parallel specimen layers.

Figure 2A:
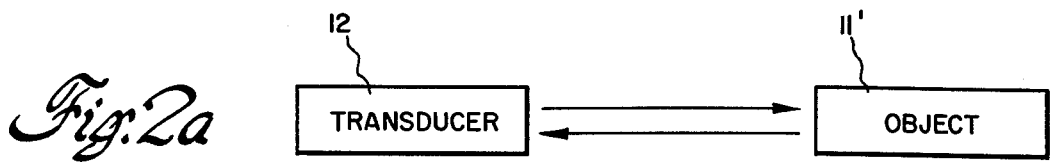
FIGS. 2a –2c illustrate a simple object and transducer the echo train of pulses $y(t)$ detected for the simple object and the computed impedance $Z(t)$.
Figure 2B:
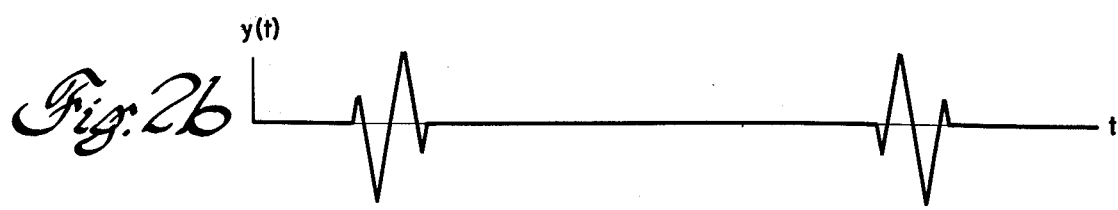
Figure 2C:
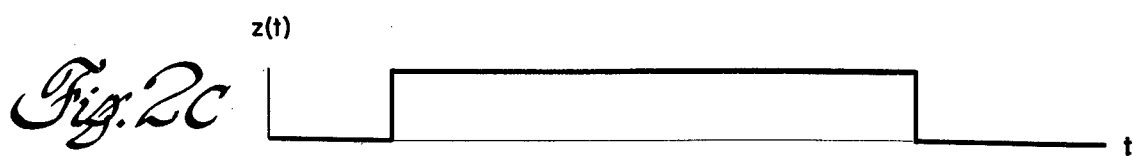

As was mentioned, echoes are reflected at acoustic impedance discontinuities in the specimen, and the amplitude of the received echoes varies with the magnitude of change in acoustic impedance. The larger is the change in acoustic impedance, the larger is the echo, and conversely if there is no change in acoustic impedance there is no echo. Going from a high to a low impedance results in a negative echo, while going from a low to a high impedance results in a positive echo. FIG. 2a shows a simple object 11', such as a long metal bar, and the resulting $y(t)$ echo trace is given in FIG. 2b. In FIG. 2c, it is seen that the acoustic impedance $Z(t)$ is uniform throughout the object. The equation for computing the line integral of $Z(t)$, which is then used as the input to the reconstruction program, will now be given.

At any depth or time $t$ within the specimen, the acoustic impedance is $Z(t) = v(t) \rho(t)$, where v is the velocity of propagation of the generated acoustic pulse, and $\rho$ is the density. This (Z) is the constitutively significant parameter of the specimen which it is desired to measure. The projection of the impedance Z, defined as a line integral of Z from the transducer to a predetermined maximum time or depth T, is given by $$P = \int_0^T Z(t)dt = T - \frac{\int_0^T t^2 y(t)\exp(\int_0^{x(t)} \alpha dx) dt}{\int_0^T t\, h(t)dt} \quad (1)$$

where $P$ is the projection, $T$ is the predetermined maximum time or depth, $t$ is the time effectively measured from the generation of an acoustic pulse, $y(t)$ is the echo signal amplitude, $\alpha$ is the predetermined acoustic loss in the specimen, $x(t)$ is the distance into the specimen, and $h(t)$ is the known system impulse response.

Figure 3:
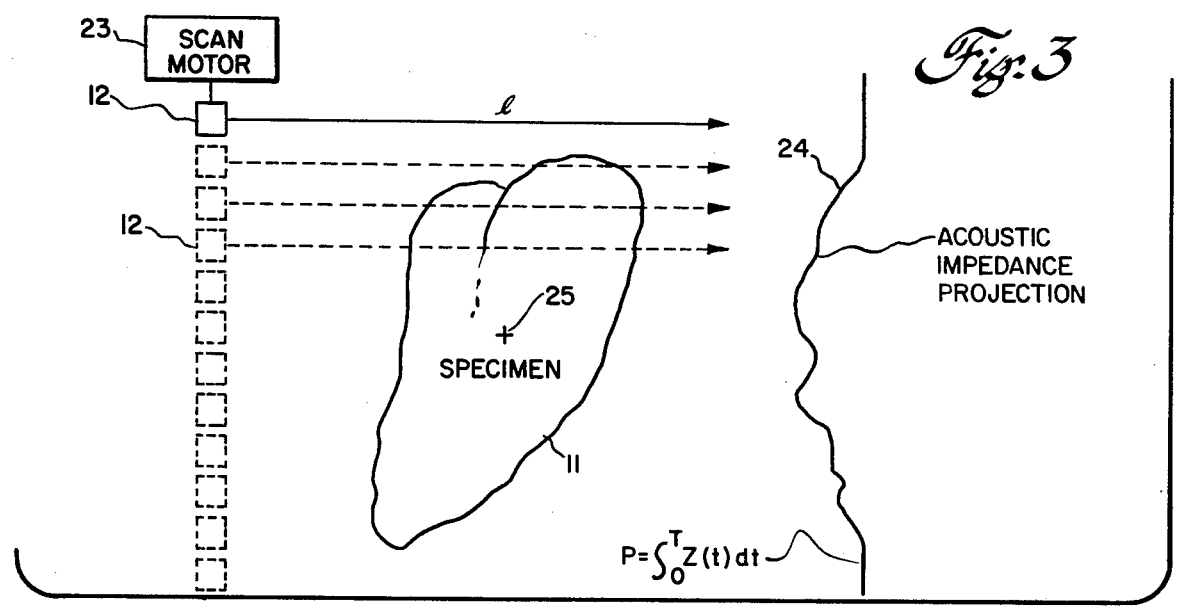
FIG. 3 is a diagrammatic top view of a scanner with a single transducer making a linear scan and further illustrating several acoustic rays and a sample impedance projection representing the line integral of the impedance along the paths l.

By analyzing the received echo signal $y(t)$ according to equation (1), the impedance projection can be derived. The significance of this is shown in FIG. 3. A simple linear scan is illustrated, in which a single electroacoustic transducer 12 is incrementally moved by a scan motor 23 to the dashed line positions. At each transducer position, transducer 12 is excited to generate an acoustic pulse and then detects the echo pulses reflected at acoustic impedance discontinuities in the specimen being examined and generates a received echo electrical signal. Along any path l from transducer to specimen, the line integral acoustic impedance along that path is determined from equation (1). As the transducer is scanned, many such projections values are calculated to form the impedance projection 24 of the specimen for a single scan angle. The tank and transducer 12 are then incrementally rotated about the rotational axis 25 to vary the angle of the scan systematically and other impedance projections, typically 100 such projections are similarly obtained.

Figure 4:
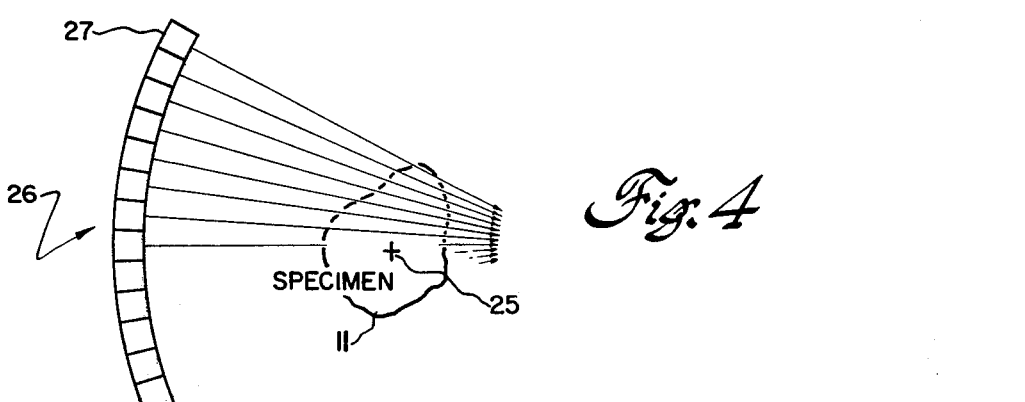
FIG. 4 is a sketch of a transducer array for a scanner with a fan beam geometry.

The linear scan depicted in FIG. 3 is analogous to a parallel scan in x-ray computerized tomography systems, and can be replaced by other geometries such as the fan beam arrangement in FIG. 4 without departing from the substance of the concept. For the fan beam geometry, an arcuate transducer array 26 is provided which is rotatable by increments about rotational axis 25 to change the scan angle. Any given scan angle, the array remains stationary and the individual transducers 27, which function as both transmitters and receivers, are operated in sequence. Each separate transducer generates an acoustic pulse and detects the reflected echoes before the next transducer in sequence is operated. If desired, a single projection analysis circuit 16 (FIG. 1) can be time-shared among transducers 27 by an appropriate switching arrangement.

In the formula for the projection P of acoustic impedance, the predetermined maximum depth or time T is explained in simpler terms as being a relatively large time beyond which no more data is received. For many specimens T is a time sufficiently large that the generated acoustic pulse emerges from the far side of the specimen and reenters the water bath. In a medical application in which the acoustic pulse enters the chest area of the body directed toward the lungs, T is the time for propagation of the acoustic pulse from the transducer to the lung wall. The loss factor in the numerator involving the integral of $\alpha dx$, where $\alpha$ is the acoustic loss in the specimen, increases as the depth into the specimen increases. A constant signal excites the transducers so that the intensity of all of the generated acoustic pulses is approximately the same, and the loss factor accounts for attenuation and other sources of loss as it propagates through the specimen. The value of $\alpha$ is known or can be estimated; for example, the loss in steel is well known, but for a medical specimen $\alpha$ will vary. The impulse response factor in the denominator involving the integral of $t\,h(t)dt$, where $h(t)$ is the known system impulse response, can also be referred to as a calibration factor and may be replaced by a constant. It will be noted that positive and negative echoes do not cancel one another, even for the simple object in FIG. 2a, because the received echo amplitude $y(t)$ is multiplied by the square of the time $t$.

Figure 5:
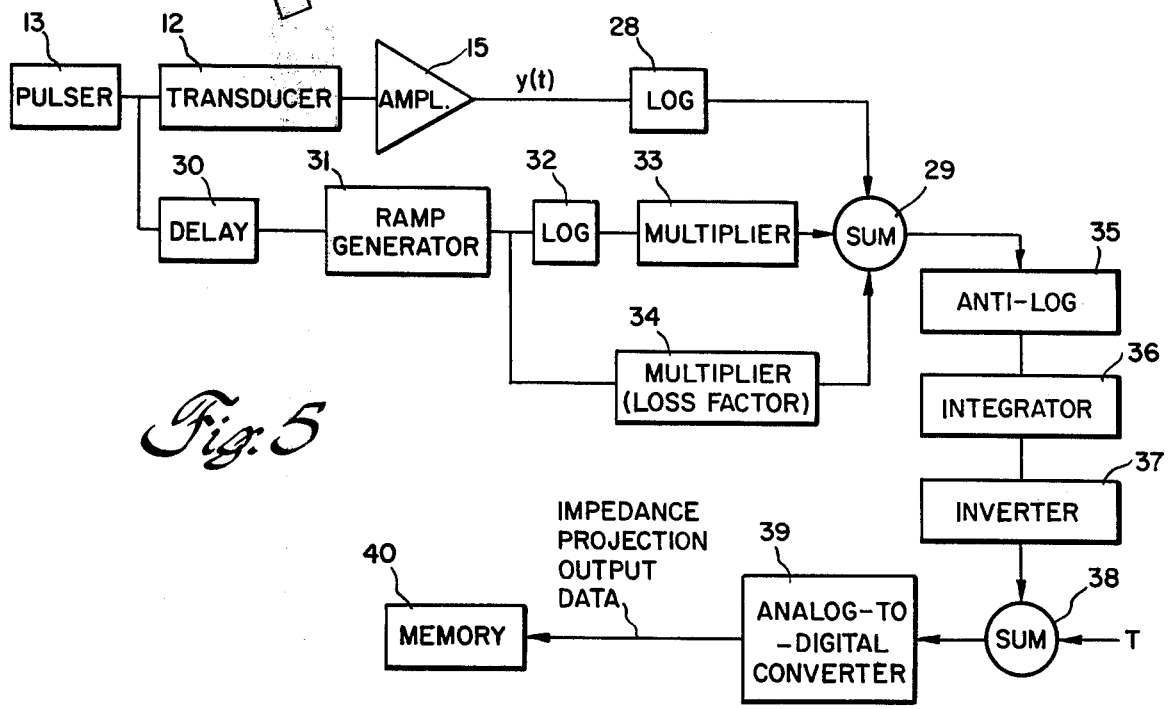
FIG. 5 is a block diagram of an analog computation circuit for computing impedance projection output data in real time.

There are a number of means for carrying out the analysis in equation (1). As was previously mentioned, one way is to digitize the received echo signal $y(t)$ and use a computer to calculate the integral. However, this would be impractical in medical applications, where the requirement is to provide the impedance projection output data directly in real time, for acquisition by the computer. The analog computation circuit in FIG. 5 embodies one technique for generating analog projection output data in real time. The analog output data is converted to digital form for storage in a separate memory unit or in the computer memory. The received echo signal $y(t)$ detected by transducer 12 is fed to amplifier 15 and then to a logarithm circuit 28 for continuously generating the natural logarithm of the echo signal, which in turn is supplied as one input to a summing circuit 29. In another branch, a transmitter timing signal is generated at the output of pulser 13 coincident with the excitation of transducer 12 and the generation of the acoustic pulse. The transmitter timing signal is applied to a delay circuit 30, and in turn to a ramp generator 31 for producing a linearly increasing time signal. During the delay interval, which may be adjustable by the operator, the acoustic pulse is travelling through the water bath and there is no received data. The natural logarithm of the linearly increasing time signal is derived in a second logarithm circuit 32, and the output is multiplied by two in a multiplier 33 and then thereafter supplied as a second input to summing circuit 29. This signal represents the term $t^2$ in equation (1). A second multiplier 34 in a parallel branch continuously multiplies the linearly increasing time signal by the predetermined acoustic loss factor, this being the third input to summing circuit 29.

The anti-logarithm of the output of summer 29 is generated in an anti-logarithm circuit 35 and represents the continuously changing product, before integration, of the three terms in the numerator of the equation. The output of integrator 36, then, is the numerator itself, and the denominator involving the system impulse response factor is not separately calculated because it is assumed to be a constant accounted for by the circuit gain. The output of integrator 36 is applied to an inverter 37 and then to a second summing circuit 38, which has as the second input the predetermined maximum time T. Thus, the computation called for in equation (1) is now completed and the output of summing circuit 38 is the impedance projection output data, in analog form, for a given acoustic pulse path. An analog-to-digital converter 39 converts the analog data to digital form for storage in a memory unit 40.

The ability to quantitatively characterize specimens with reflective ultrasound leads to a variety of medical and industrial applications such as whole body medical imaging and laminography, and the nondestructive testing of metal parts. The determination of a numeric or quantitative value of acoustic impedance at a known location in the slice being imaged is expected to lead to medically useful information. For instance, it is expected that cancerous tissues will have a higher acoustic impedance than normal tissue. Ultrasonic inspection of metal parts by this technique will reveal unexpected variations in the density of the metal or in acoustic velocity.

While the invention has been particularly shown and described with reference to several preferred embodiments thereof, it will be understood by those skilled in the art that various changes in form and details may be made therein without departing from the spirit and scope of the invention.

The invention claimed is:

1. A method of producing acoustic impedance projections for computerized reflective ultrasonic imaging comprising the steps of exciting at least one electroacoustic transducer to generate a series of acoustic pulses directed toward a specimen being examined and propagating along multiple paths sufficient to scan the specimen for a single projection, detecting for each path the echo pulses reflected at acoustic impedance discontinuities in the specimen to thereby generate a received echo electrical signal, computing impedance projection output data representing the line integral of the acoustic impedance along each path utilizing the amplitude of the received echo signals, and repeating the foregoing steps at multiple scan angles, with respect to a rotational axis, of the specimen relative to the excited transducer to derive additional sets of impedance projection output data for an ensemble of projections to be used in combination to reconstruct impedance distributions at known coordinates in a specimen layer.

2. The method according to claim 1 wherein the impedance projection output data is computed by the equation $$P = \int_0^T Z(t)dt = T - \frac{\int_0^T t^2 y(t) \exp\left(\int_0^{x(t)} \alpha dx\right) dt}{\int_0^T t\, h(t)dt},$$

where P is the projection, T is a predetermined maximum time or depth, t is the time effectively measured from the generation of an acoustic pulse, y(t) is the echo signal amplitude, α is the acoustic loss in the specimen, x is the distance in the specimen, and h(t) is the known system impulse response.

3. The method according to claim 2 further including the step of translating the specimen and said at least one electroacoustic acoustic transducer relative to one another in the direction of the rotational axis and repeating all the foregoing steps to generate an ensemble of impedance projection output data to be used to reconstruct impedance distributions in a parallel specimen layer.

4. The method according to claim 3 further including the step of storing said impedance projection output data in a memory.

5. A method of producing acoustic impedance projections for computerized reflective ultrasonic imaging comprising the steps of
    exciting an electroacoustic transducer to generate an acoustic pulse directed toward a specimen being examined and detecting the echo pulses reflected at acoustic impedance discontinuities to thereby generate a received echo electrical signal,
    repeating the foregoing steps to generate a plurality of received echo signal for acoustic pulses propagating along multiple paths through the specimen sufficient to scan the specimen for a single projection,
    generating transmitter timing signals effectively measured from the generation of said acoustic pulses,
    computing impedance projection output data representing the line integral of the acoustic impedance along each path using the received echo signal amplitude, the square of time derived from said timing signals, a known loss factor which increases as the depth into the specimen increases, a known impulse response factor, and a preselected maximum time and upper limit of integration, and
    repeating the foregoing steps at multiple scan angles, with respect to the rotational axis, of the specimen relative to the excited transducer to generate additional sets of impedance projection output data to be used in combination to reconstruct impedance distributions at known coordinates in a specimen layer.

6. The method according to claim 5 wherein the step of computing impedance projection output data comprises supplying said received echo signal and transmitter timing signal to an analog computation circuit which generates said projection output data in analog form.

7. The method according to claim 6 further including the steps of converting said projection output data in analog form to digital form and storing in a memory.

8. The method according to claim 6 further including the step of translating the specimen and said at least one electroacoustic transducer relative to one another in the direction of the rotational axis and repeating all of the foregoing steps to generate an ensemble of impedance projection output data to be used to reconstruct impedance distributions in a parallel specimen layer.

9. Apparatus for reflective ultrasonic imaging by computerized reconstruction of impedance projections comprising
    a scanner having a rotational axis and including a liquid tank on which is supported electroacoustic transducer means,
    means for sequentially exciting said transducer means to generate a series of acoustic pulses which propagate along multiple paths through a specimen in the liquid tank being examined and which are sufficient to scan the specimen for a single projection, said transducer means detecting the echo pulses reflected at acoustic impedance discontinuities in the specimen and generating a received echo electrical signal for each path, and means for producing a transmitter timing signal actuated by excitation of said transducer means, and
    computation circuit means for processing said received echo and transmitter timing signals and for computing impedance projection output data representing the line integral of the acoustic impedance along each path utilizing the amplitude of the received echo signals,
    said scanner further including means for incrementally rotating said liquid tank and transducer means relative to the specimen, whereby additional sets of impedance projection output data can be generated to be used in combination to reconstruct impedance distributions at known coordinates in a specimen layer.

10. The apparatus according to claim 9 wherein said computation circuit means computes the impedance projection output data by the equation $$P = T - \frac{\int_0^T t^2 y(t) \exp\left(\int_0^{x(t)} \alpha dx\right) dt}{\int_0^T t\, h(t)dt},$$

where P is the projection, T is a predetermined maximum time, t is the time effectively measured from excitation of said transducer means, y(t) is the received echo signal amplitude, α is the predetermined acoustic loss in the specimen, x is the distance into the specimen, and h(t) is the system impulse response.

11. The apparatus according to claim 10 wherein said computation circuit means is an analog computation circuit for generating the projection output data in analog form, means for converting the analog projection output data to digital form, and a memory for storing the digital projection output data.

12. The apparatus according to claim 10 wherein said computation circuit means is an analog computation circuit comprising first means for deriving the logarithm of said received echo signal, a delay circuit actuated by said transmitter timing signal, a ramp generator actuated by the output of said delay circuit and producing a linearly increasing time signal, second means for deriving the logarithm of said linearly increasing time signal and multiplying the logarithm by two, third means for multiplying said linearly increasing time signal by the acoustic loss, a first summing circuit for summing the outputs of said first, second, and third means, fourth means for deriving the anti-logarithm of the output of said first summing circuit, an integrator circuit for integrating the output of said fourth means, fifth means for inverting the output of said integrator circuit, and a second summing circuit for summing the maximum time T and the output of said fifth means.

13. The apparatus according to claim 10 wherein said scanner further includes means for translating said tank and transducer means incrementally in the direction of the rotational axis, whereby impedance projection output data can be generated in a plurality of axial positions to be used to reconstruct impedance distributions for a plurality of parallel specimen layers.

14. The apparatus according to claim 10 wherein said transducer means is comprised by a single transducer, and means for incrementally moving said transducer along a predetermined scan path while alternately generating an acoustic pulse and detecting the reflected echo pulses.

15. The apparatus according to claim 10 wherein said transducer means is comprised by a transducer array, the individual transducers in said array being operated in sequence to generate an acoustic pulse and detect the reflected echo pulses.

* * * * *